(12) United States Patent
Krishnaswamy et al.

(10) Patent No.: US 10,646,165 B2
(45) Date of Patent: May 12, 2020

(54) REMOVING ELETROPHYSICOLOGIC ARTIFACTS FROM A MAGNETIC RESONANCE IMAGING SYSTEM

(71) Applicant: THE GENERAL HOSPITAL CORPORATION, Boston, MA (US)

(72) Inventors: Pavitra Krishnaswamy, Boston, MA (US); Patrick L. Purdon, Somerville, MA (US); Emery N. Brown, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 1150 days.

(21) Appl. No.: 14/782,479

(22) PCT Filed: Apr. 10, 2014

(86) PCT No.: PCT/US2014/033619
§ 371 (c)(1),
(2) Date: Oct. 5, 2015

(87) PCT Pub. No.: WO2014/169100
PCT Pub. Date: Oct. 16, 2014

(65) Prior Publication Data
US 2016/0038091 A1    Feb. 11, 2016

Related U.S. Application Data

(60) Provisional application No. 61/810,475, filed on Apr. 10, 2013.

(51) Int. Cl.
*A61B 5/0476*    (2006.01)
*A61B 5/00*    (2006.01)
(Continued)

(52) U.S. Cl.
CPC ............ *A61B 5/7203* (2013.01); *A61B 5/024* (2013.01); *A61B 5/0476* (2013.01); *A61B 5/055* (2013.01);
(Continued)

(58) Field of Classification Search
CPC ............ A61B 5/04004; A61B 5/04017; A61B 5/4094; A61B 5/0476; A61B 5/02405;
(Continued)

(56) References Cited

U.S. PATENT DOCUMENTS 4,911,167 A    3/1990    Corenman et al.
5,195,530 A    3/1993    Shindel
(Continued)

FOREIGN PATENT DOCUMENTS

WO    2012/145285 A1    10/2012

OTHER PUBLICATIONS

International Search Report and Written Opinion dated Sep. 23, 2014 in connection with PCT/US2014/33619.
(Continued)

*Primary Examiner* — Elmer M Chao
(74) *Attorney, Agent, or Firm* — Quarles & Brady LLP

(57) ABSTRACT

Systems and a method for reducing periodic artifacts in an electrophysiologic signal are provided. The method includes receiving a time-series electrophysiologic signal acquired from a subject and providing a regression model that defines an interference signal caused by periodic artifacts using a harmonic representation. The method also includes applying the regression model using the time-series electrophysiologic signal to define a cost function and performing an iterative optimization process to estimate regression parameters that minimize the cost function. The method further includes determining, using the regression parameters, the interference signal, and generating a corrected time-series
(Continued)

electrophysiologic signal by reducing the interference signal.

20 Claims, 8 Drawing Sheets

(51) Int. Cl.
    *A61B 5/055*     (2006.01)
    *A61B 5/11*     (2006.01)
    *A61B 5/024*     (2006.01)

(52) U.S. Cl.
    CPC ........... *A61B 5/1102* (2013.01); *A61B 5/4064* (2013.01); *A61B 2576/026* (2013.01)

(58) Field of Classification Search
    CPC . A61B 5/02416; A61B 5/0816; A61B 5/7207; A61B 5/7253; A61B 5/7257; A61B 5/0823; A61B 5/1455; A61B 5/6814; A61B 5/721; A61B 5/1102
    See application file for complete search history.

(56) References Cited

U.S. PATENT DOCUMENTS

| | | |
|---|---|---|
| 6,944,565 B2 | 9/2005 | McNeilage et al. |
| 7,286,871 B2 | 10/2007 | Cohen |
| 8,298,154 B2 | 10/2012 | Hete et al. |
| 2008/0306397 A1 | 12/2008 | Bonmassar et al. |
| 2011/0044524 A1 | 2/2011 | Wang et al. |

OTHER PUBLICATIONS

Lin, Ct., et al. EEG-Based Drowsiness Estimation for Safety Driving Using Independent Component Analysis, IEEE Transactions On Cricuits and Systems, Dec. 2006; vol. 52, No. 12, pp. 2726-2738; p. 2733; section C.

Blanco, S. et al. Time-frequency analysis of electroencephalogram series III. Wavelet packets and information cost function, Physical Review E. Jan. 1998; vol. 57, No. 1; pp. 932-940; p. 936; section C.

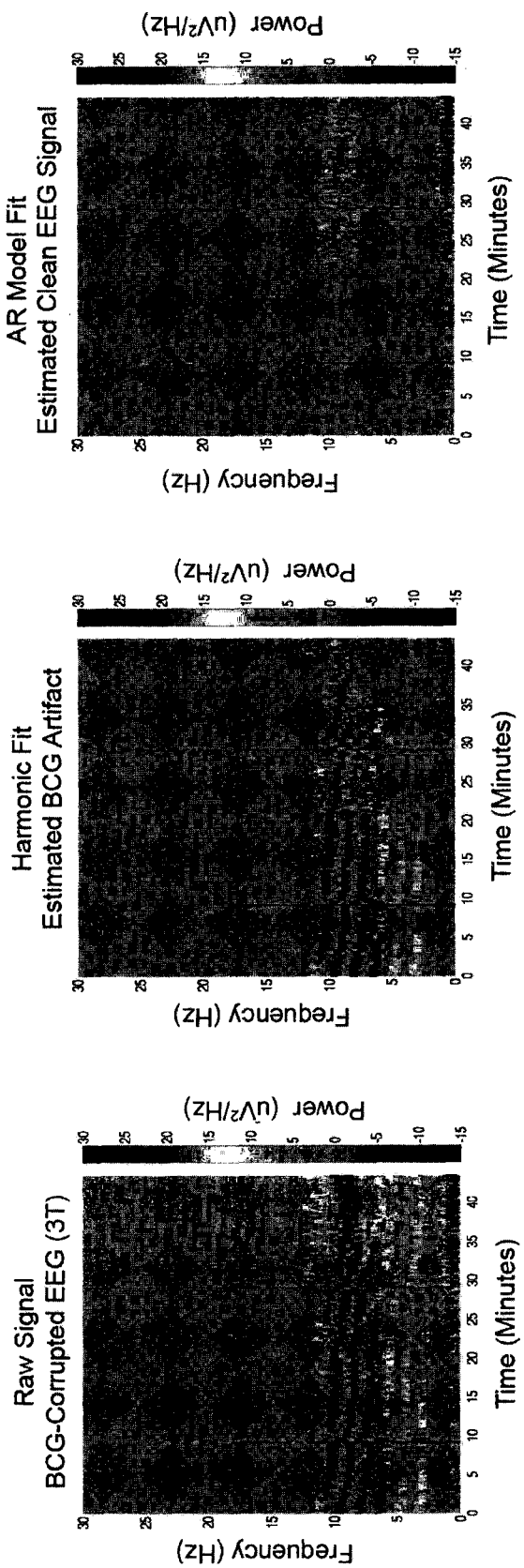

REMOVING ELETROPHYSICOLOGIC ARTIFACTS FROM A MAGNETIC RESONANCE IMAGING SYSTEM

CROSS-REFERENCE TO RELATED APPLICATIONS

This application represents the national stage entry of PCT International Application No. PCT/US2014/033619 filed Apr. 10, 2014, which claims priority to and incorporates herein by reference in its entirety U.S. Provisional Patent Application Ser. No. 61/810,475 filed Apr. 10, 2013, the contents of which are hereby incorporated by reference in their entirety for all purposes.

GOVERNMENT RIGHTS

This invention was made with government support under grant No. R01-EB006385 and grant No. DP2-OD006454 awarded by the National Institutes of Health. The government has certain rights in the invention.

BACKGROUND

The present disclosure relates generally to systems and methods for monitoring electrophysiologic information from a subject or patient, and, in particular, to systems and methods for removing artifacts from electrophysiologic information generated in relation to magnetic resonance imaging ("MRI") systems.

Electrophysiologic recordings, such as electroencephalography ("EEG"), electrocardiography ("ECG") or galvanic skin response ("GSR"), conducted in an MRI scanner offer a useful means to enhance the utility of MRI measurements. In the specific instance of brain function assessment, EEG recordings supply brain activity information with a high temporal resolution. When combined with high spatial resolution, soft tissue resolution and biochemical versatility of MRI measurements, as provided by functional magnetic resonance imaging with blood oxygen level-dependent ("fMRI-BOLD") contrast or arterial spin labeling ("ASL"), synchronous examination of brain function across spatial and temporal scales may be achieved. Correlating haemodynamic changes in brain with concomitant electrophysiologic signatures offers enhanced potential to monitor brain function in normal, clinical and pathological states. For example, the goal of identifying brain regions generating a known electrophysiologic signature, such as an epileptic discharge, necessitates resolving both millisecond-scale electrical signatures (only measurable with EEG) with millimeter-scale brain areas with increased activity (only measurable on fMRI) concomitantly. This kind of brain function assessment is known as electroencephalography-correlated fMRI ("EEG-fMRI"). Generally, additional electrophysiologic signals are also acquired during MRI scanning, which include respiratory or cardiac function measurements, thus providing complementary information to the MRI assessment of physiologic parameters under study.

The utility of these techniques, however, is fundamentally limited by the presence of magnetic fields and gradients in the MRI scanner, along with radiofrequency ("RF") signals transmitted and received during imaging. These features of the MR-environment introduce artifacts in electrophysiologic recordings conducted within the MR scanner. As an example of MR environment related artifacts in electrophysiologic recordings, ballistocardiogram ("BCG") artifacts are induced in brain EEG recordings on account of motion of head and scalp electrodes, primarily due to cardiac and blood flow pulsatile movements, within the magnetic field of the scanner. In particular, BCG artifacts have significantly larger amplitudes (150-200 microVolts at 1.5 Tesla) than underlying EEG activity (10-100 microVolts), and so EEG activity can be obscured up to 20 Hz, lowering specificity and sensitivity of the EEG recordings acquired in proximity to an MRI scanner. Moreover, additional complications arise from the fact that changes in heart rate, blood pressure and resulting pulsatile head motion cause variations in the shape, timing and intensity of the BCG artifacts, making predictability and removal of BCG artifacts very challenging.

Several attempts to remove BCG artifacts from EEGs have been previously reported. For example, a common approach includes measurement of a reference signal obtained from electrocardiograms ("ECG") or motion sensors. The reference signal is used to generate a waveform template that defines an estimate for BCG artifacts, which is then subtracted from contaminated EEG measurements to produce corrected EEG signals. However, this approach relies on high quality ECG or motion data in order to robustly perform peak detection and/or adaptive filtering, which becomes particularly difficult in magnetic fields greater than 1.5 Tesla or during long EEG recordings, since reference signals acquired in a MRI scanner are also often corrupted.

In addition, some reference signal-free BCG removal methods, such as independent component analysis and wavelet basis decompositions, have also been explored. These approaches rely on the separability between true EEG signals and BCG artifacts with respect to signal amplitude, time and/or frequency. However, many basis elements often contain substantial overlap between signals and artifacts in these domains. This skews the separation, and necessitates subjective and case-specific criteria to define which basis elements may be excluded as "artifact" and which ones may be retained as "true EEG signal." In addition, such criteria demand significant post-algorithmic-processing.

The above limitations make current methods inadequate for providing the quality of measurements required for monitoring or investigating brain function for cognitive studies and clinical applications. Thus, there is a need for systems and methods that do not require reference signals or subjective separation criteria for removing artifacts from electrophysiologic measurements acquired in a MRI scanner.

SUMMARY

The present invention overcomes aforementioned drawbacks by providing systems and methods for reducing artifacts from electrophysiologic signals, such as EEG signals, acquired from a subject positioned within a magnetic resonance imaging ("MRI") scanner. In particular, a harmonic regression technique is provided that includes physically motivated parametric models of artifacts and underlying physiological signals. The present invention provides an iterative optimization process to identify model parameters, and estimate corrupting artifacts contained in such signals. This approach affords accurate artifact removal and enables successful recovery of true electrophysiologic signatures, such as EEG signatures, as obtainable outside a MRI scanner.

In accordance with one aspect of the disclosure, a magnetic resonance imaging ("MRI") system is provided. The MRI system includes a magnet system configured to generate a polarizing magnetic field about a portion of the subject positioned in the MRI system and a plurality of gradient coils configured to apply a gradient field to the polarizing magnetic field. The MRI system also includes a radio frequency (RF) system configured to apply a RF excitation field to the subject, and acquire therefrom a set of magnetic resonance image ("MRI") data, and at least one input configured to receive electrophysiologic data acquired from the subject. The MRI system further includes at least one computer configured to process the electrophysiologic data as a time-series signal and apply a regression model that defines an interference signal caused by artifacts in the time-series signal using a harmonic representation to define a cost function. The at least one computer is also configured to perform an iterative optimization process to estimate regression parameters that minimize the cost function and determine, using the regression parameters, the interference signal. The at least one computer is further configured to and generate a corrected time-series electrophysiologic signal by reducing the interference signal relative to the time-series electrophysiologic signal.

In accordance with another aspect of the disclosure, a system for monitoring a subject's brain is provided. The system includes an input configured to receive electroencephalogram ("EEG") data acquired from a subject, and at least one processor configured to receive the EEG data from the input and apply a regression model that defines a ballistocardiogram signal using a harmonic representation to the EEG data to define a cost function. The at least one processor also configured to perform an iterative optimization process to estimate regression parameters that reduce the cost function and determine, using the regression parameters, the ballistocardiogram signal. The at least one processor is further configured to generate a corrected EEG data by reducing the ballistocardiogram signal within the EEG data. The system also includes an output configured to deliver a report representative of the corrected EEG data.

In accordance with yet another aspect of the disclosure, a method for reducing artifacts in an electroephysiologic signal is provided. The method includes receiving a time-series electrophysiologic signal acquired from a subject and providing a regression model that defines an interference signal caused by periodic artifacts using a harmonic representation. The method also includes applying the regression model using the time-series electrophysiologic signal to define a cost function and performing an iterative optimization process to estimate regression parameters that minimize the cost function. The method further includes determining, using the regression parameters, the interference signal, and generating a corrected time-series electrophysiologic signal by reducing the interference signal.

The foregoing and other advantages of the invention will appear from the following description.

BRIEF DESCRIPTION OF THE DRAWINGS

FIG. 3A-3C are graphical illustrations comparing example spectrograms of corrupted EEG signals (FIG. 3A), BCG artifacts (FIG. 3B) and corrected EEG signals after removal of BCG artifacts (FIG. 3C), in accordance with the present invention.

DETAILED DESCRIPTION

Obtaining high quality electrophysiologic signals, in combination with medical imaging, such as MRI measurements, is important for studies of physiologic and clinical states. For instance, obtaining electroencephalogram ("EEG") recordings concomitantly with MRI measurements is important for examination of brain dynamics in cognitive and clinical states such as sleep, attention, coma, anesthesia, and epilepsy, but often necessitates overcoming artifacts induced in the electrophysiologic signals due to interference from the medical imaging device, such as an MRI scanner. In particular, ballistocardiogram ("BCG") artifacts are induced in EEG recordings on account of motion of head and scalp electrodes within the magnetic field of the MRI scanner.

Figure 1C:
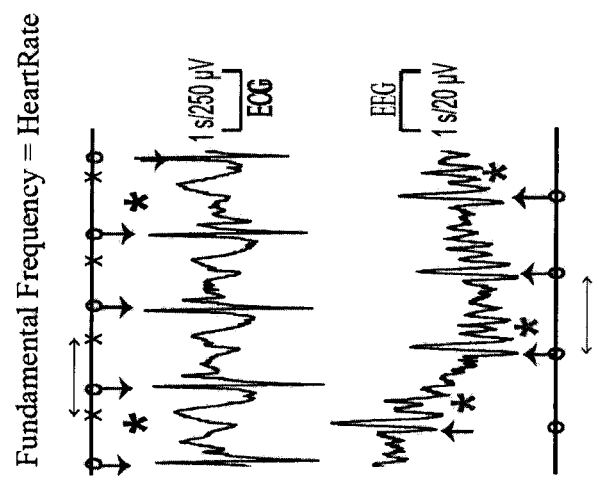
FIG. 1C is a graphical illustration comparing EEG time-series data corrupted by BCG artifacts and concomitant electrocardiogram ("ECG") time-series data.
Figure 1B:
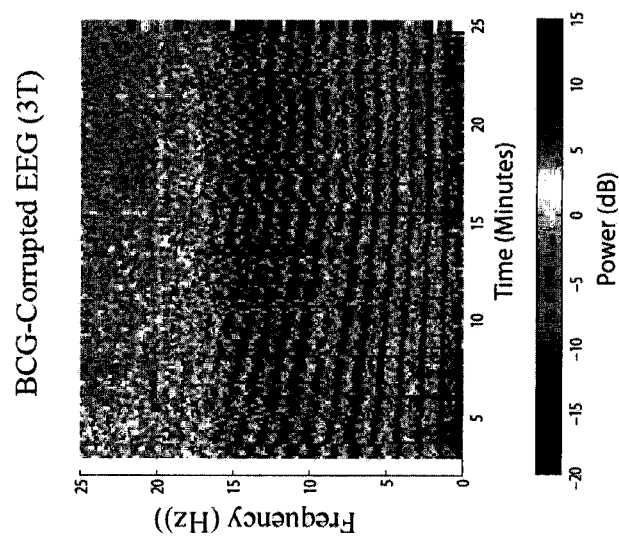
FIG. 1B is a graphical illustration depicting the spectral signature of the example EEG signal of FIG. 1A contaminated by ballistocardiogram ("BCG") artifacts generated within an MRI scanner using similar GA protocol as in FIG. 1A.
Figure 1A:
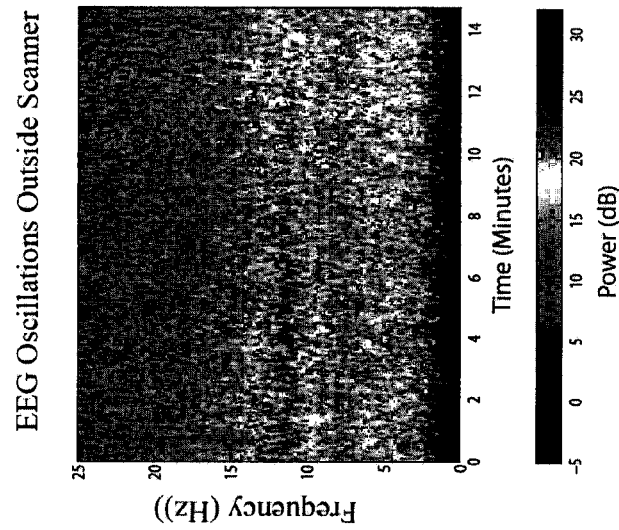
FIG. 1A is a graphical illustration depicting the spectral signature of an example electroencephalogram ("EEG") signal recorded outside a magnetic resonance imaging ("MRI") scanner during general anesthesia ("GA").

In contrast to previous methods that rely on cardiac or motion reference signals, which are often corrupted or difficult to acquire, the present disclosure recognizes that a natural harmonic basis may be used to describe BCG artifacts in an approach that obviates the need for acquiring reference signals. This can be appreciated in the example of FIG. 1, which illustrates a comparison between spectral signatures of BCG-free (FIG. 1A) and BCG-corrupted (FIG. 1B) EEG signals. Specifically, FIG. 1A shows an example of an oscillatory EEG signal that is a spectral signature of loss of consciousness under general anesthesia. Similar oscillatory signatures are observed in a variety of cognitive and clinical brain states. On the other hand, FIG. 1B depicts the spectral signature in EEG acquired during loss of consciousness under general anesthesia in an MR scanner at 3 Tesla. In particular, it can be seen that the BCG-corrupted EEG signal comprises a series of harmonic streaks, that overpower the underlying EEG oscillatory spectral signatures of interest. The harmonic feature is also reflected in the time domain data, which is dominated by pulsatile (comb-like) BCG occurrences coincident with a heart rate period (FIG. 1C).

As will be described, a regression model that captures physical and physiological features of BCG artifacts, and underlying EEG signals, is introduced. However, such approach is not limited to BCG artifacts in EEG, and may be applicable to any electrophysiologic signals corrupted by periodic artifacts. Specifically, the temporal structure of BCG artifacts may be modeled using harmonic series, while oscillatory dynamics of true EEG signals may be defined using an autoregressive ("AR") series. Since such a regression model specifies the template for the BCG, there is no explicit need for acquiring reference signals. Furthermore, the parametric model forms are specific, yet flexible enough to be generalizable, and objective while taking the character of the data, and hence do not require subjective or case-specific criteria to deal with the time-frequency overlap between the electrophysiologic signal of interest and the MR-environment related artifact. Estimating and removing BCG artifacts then becomes a problem of identifying the regression parameters for the harmonic and AR models to best explain the contaminated EEG data recorded in the scanner. In particular, an iterative optimization process may then be used, by way of a maximum likelihood technique, to compute model parameters and determine BCG artifacts, facilitating accurate removal of artifacts from corrupted EEG measurements.

As mentioned, BCG-corrupted EEG signals can be described by a sum of the BCG artifact signals and underlying EEG signals. Specifically, a BCG-corrupted EEG signal may be defined using a harmonic series and oscillatory EEG signal model. Denoting the BCG-corrupted EEG oscillations from any given channel as the "measured" data series $y_1, y_2, \ldots, y_T$ it follows that:

$$y_t = s_t + v_t \quad (1)$$

In Eqn. 1, $s_t$ is the BCG artifact modeled as an $N^{th}$ order harmonic series, namely:

$$s_t = \mu_0 + \mu_1 t + \sum_{r=1}^{N} A_r \cos(\omega r t) + B_r \sin(\omega r t) \quad (2)$$

where N is the number of harmonics in the spectrum, and $\omega$ (rad/sec) is the fundamental frequency defining the harmonic template, which may be linked to a heart rate in Hz (as shown in FIG. 1C). In addition, $A_r$ and $B_r$ describe the amplitude and phase of $r^{th}$ harmonic.

In Eqn. 1, $v_t$ is the oscillatory electrophysiologic signature in the EEG modeled using a $P^{th}$ order autoregressive ("AR") representation, namely:

$$v_t = \sum_{k=1}^{P} a_k v_{t-k} + \in_t \quad (3)$$

where P may be set based on information criteria, such as the Bayesian Information Criteria, to represent the number of spectral peaks and the nature of oscillatory signatures being modeled. The $\in_t$s may be independent Gaussian random variables with zero mean and variance $\sigma_\in^2$. The AR model allows capture of oscillatory dynamics of interest in the EEG without biasing the method towards activity in any specific frequency bands.

The harmonic BCG and the autoregressive EEG models reflect the empirically observed overlap in spectral and amplitude features, but are distinct enough to decouple the BCG artifact from the true EEG test signal. With this model, the problem of estimating and removing the BCG artifact becomes one of identifying the parameters $$\omega, \beta = [\mu_0, \mu_1, A_1, B_1, A_2, B_2, \ldots \ldots A_N, B_N]^T, \alpha = [a_1, a_2, \ldots, a_P]^T, \text{ and } \sigma_\in^2.$$

The estimation problem, as set forth in Eqns. 1-3 is essentially a harmonic regression in the setting of correlated noise, which may be seen by rewriting the above model in regressor matrix notation:

$$y = Z(\omega)\beta + v \quad (4)$$

where $y = [y_{t_1}, y_{t_2}, \ldots, y_{t_T}]^T$, $s = Z(\omega)\beta$, and $Z(\omega)$ is:

$$\begin{bmatrix} 1 & \cos(\omega t_1) & \sin(\omega t_1) & \ldots & \cos(N\omega t_1) & \sin(N\omega t_1) \\ 1 & \cos(\omega t_2) & \sin(\omega t_2) & \ldots & \cos(N\omega t_2) & \sin(N\omega t_2) \\ \vdots & \vdots & \vdots & \ddots & \vdots & \vdots \\ 1 & \cos(\omega t_r) & \sin(\omega t_r) & \ldots & \cos(N\omega t_r) & \sin(N\omega t_r) \end{bmatrix}$$

and $v = [v_{t_1}, v_{t_2}, \ldots, v_{t_T}]^T$ is multivariate Gaussian (0 mean, AR covariance $Q_{T \times T}$) with an Akaike Markovian form:

$$\begin{bmatrix} v_{t-1} \\ v_{t-2} \\ \vdots \\ v_{t-P} \end{bmatrix} = \begin{bmatrix} a_1 & a_2 & \ldots & a_P \\ 1 & 0 & \ldots & 0 \\ \vdots & \ddots & \ddots & \vdots \\ 0 & \ldots & 1 & 0 \end{bmatrix} \begin{bmatrix} v_{t-2} \\ v_{t-3} \\ \vdots \\ v_{t-P-1} \end{bmatrix} + \begin{bmatrix} \in_{t-1} \\ \in_{t-2} \\ \vdots \\ \in_{t-P} \end{bmatrix} \quad (5)$$

Maximum likelihood cost functions are suitable for such parametric estimation problems. Based on a maximum likelihood criterion, the best parameter estimates are those that, for an observed T×1 data vector y, minimize:

$$-2\log L(\omega, \beta, \alpha, \sigma_\in^2 \mid y) = T\log(\sigma_\in^2) + \log(|Q|) + \frac{S_T}{\sigma_\in^2} \quad (6)$$

where $S_T = (y - Z(\omega)\beta)^T Q^{-1}(y - Z(\omega)\beta)$ and Q is the covariance matrix for the autoregressive term v and Z is as defined in Eqn. 4. Maximizing over $\sigma_\in^2$ gives the concentrated likelihood cost C to minimize:

$$C(\omega, \beta, \alpha \mid y) = T\log\left(\frac{S_T}{T}\right) + \log(\det(Q)) + N \quad (7)$$

In some aspects, minimization of Eqn. 7 can be implemented in an iterative optimization process using, for example, a cyclic descent based on Newton's method to break down the complex nonlinear optimization into a series of sub-problems, which when solved, converge to a global optimum. For a given $\alpha = \tilde{\alpha}$ and $\omega = \tilde{\omega}$, a best estimate $\hat{\beta} = \arg\min C(\beta, \tilde{\alpha}, \tilde{\omega} \mid y)$, may be given by performing a generalized least squares technique on Eqn. 4:

$$\hat{\beta}(\tilde{\alpha}, \tilde{\omega}) = [Z^T(\tilde{\omega})Q^{(-1)}Z(\tilde{\omega})]^{(-1)} Z^T(\tilde{\omega})Q^{(-1)} y \quad (8)$$

$$= [Z^*(\tilde{\omega})^T Z^*(\tilde{\omega})]^{(-1)} Z^*(\tilde{\omega})^T y^* \quad (9)$$

$$\hat{S}_T(\hat{\beta}, \tilde{\omega}) = (y^* - Z^*(\tilde{\omega})\hat{\beta})^T (y^* - Z^*(\tilde{\omega})\hat{\beta}) \quad (10)$$

where Eqns. 9-10 are obtained by factorizing $Q^{(-1)}$ as $L^T L$ and denoting $Z^* = LZ$, $y^* = Ly$. Substituting $\hat{S}_T(\hat{\beta}, \omega)$ into Eqn. 7 concentrates the likelihood over $\beta$:

$$\bar{C}(\tilde{\alpha}, \tilde{\omega} | y) = T \log\left(\frac{\hat{S}_T(\hat{b}, \omega)}{T}\right) + \log(\det(Q)) \quad (11)$$

For a given $\tilde{\alpha}$ and $\tilde{\omega}$, computing the cost (Eqns. 8-11) necessitates computation of $y^*$, $Z^*$, $\det(Q) = |Q|$. This can be done efficiently using an estimation approach adapted for the harmonic plus AR(p) model—as described by Eqn. 4. In one instance of such an estimation approach, a Kalman filter technique can be used to avoid explicit matrix multiplications, inverses and orthogonalizations. Denoting $M = [Z(\tilde{\omega}) y]$ and $M^* = [Z^*(\tilde{\omega}) y^*]$. For $j = 1, \ldots, 2N+2$, $m^* = j^{th}$ column $M^*$ can be computed by defining an observation vector $m = j^{th}$ column of a $P \times 1$ state vector $\theta_t$ and state space model:

$$\theta_t = A(\tilde{\alpha})\theta_{t-1} + N(0, I_{P \times P}) \text{ and } m_t = B\theta_t \quad (12)$$

where $A$ is the $P \times P$ matrix in Eqn. 5 and $B = [1, 0, \ldots, 0]$. Denoting the predicted state estimate and estimate covariance for the Kalman filter as $\theta_{t|t-1}$ and $P_{t|t-1}$, it follows:

$$|Q| = \prod_{t=1}^{T} BP_{t|t-1} \text{ and } m_t^* = \frac{(m_t - B\theta_{t|t-1})}{\sqrt{BP_{t|t-1}}} \quad (13)$$

Running this filter across all $j$ gives $y^*$, $Z^*$ and $|Q|$, and substituting these into Eqns. 8-11 gives the cost $\bar{C}$ to minimize.

The numerical optimization of $\bar{C}$ over $\alpha$ and $\omega$ is well-defined to have a unique solution and thus may be implemented using a variety of optimization routines. The optimization requires denoting bounds on the search space for $\omega$ and $\alpha$. The $\omega$ search space may be physiologically bounded, for example, using a subject's clinical heart rate range. Bounds for $\alpha$ values may also be set to any desired range, such as between 0.2 and 5 times the AR coefficients obtained by fitting the full data vector $y$ to an AR model (Eqn. 3).

The numerical optimization of $\bar{C}$ over $\alpha$ and $w$ may then be used to re-evaluate Eqns. 8-13 to get the associated optimal $\hat{\beta}$ and $\hat{S}_T$. Lastly, Eqn. 7 gives the optimal $$\hat{\sigma}_\epsilon^2 = \frac{\hat{S}_T}{T}.$$

The above maximum likelihood approach may be applied segment by segment on any amount of BCG-corrupted EEG data $y$ to obtain model parameter estimates $\hat{\omega}$, $\hat{\beta}$, $\hat{\alpha}$, $\hat{\sigma}_\epsilon^2$. With these estimated parameters, estimates for the BCG artifacts ($\hat{s}_t$), EEG oscillation ($\hat{v}_t$) and residual noise ($\hat{\epsilon}_t$) time series may be computed.

Figure 2:
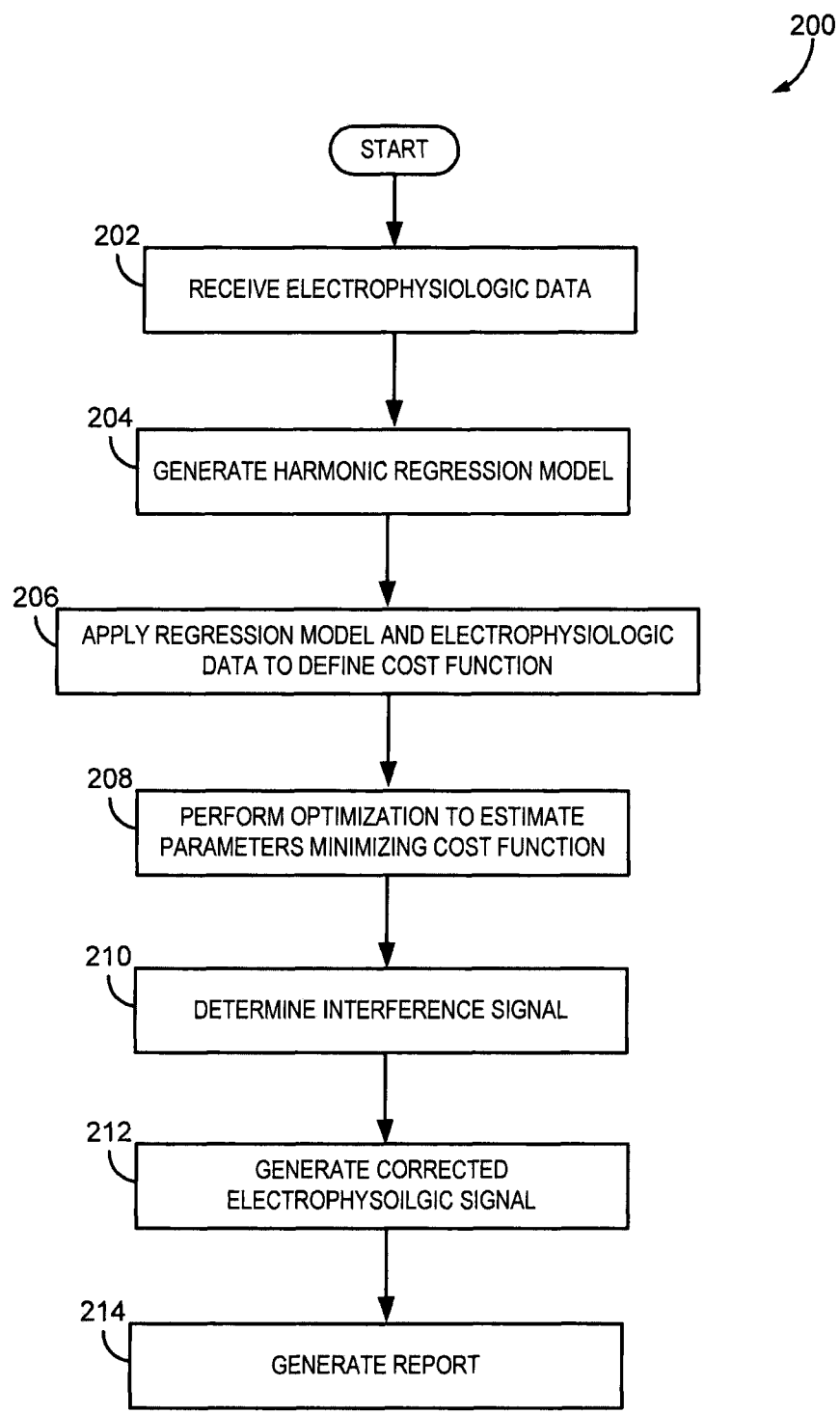
FIG. 2 is a flowchart setting forth the steps of a process in accordance with the present invention.

Turning to FIG. 2, a flowchart setting forth the steps of a process 200 in accordance with the present invention is shown. The process 200 begins at process block 202 where any amount of electrophysiologic data contaminated by periodic artifacts, such as EEG data containing BCG artifacts induced by an environment of a MRI scanner, may be received. In some aspects, the electrophysiologic data may be acquired, either intermittently or in real-time, by way of any number of sensors arranged as desired on a subject. The sensors may be configured to acquire and process electrophysiologic data, and may be either integrated into, in communication with, or configured in parallel with an MRI system or any other acquisition system(s). Additional data may also be acquired at process block 202, such as fMRI or other MRI data, electrocardiogram ("ECG") data, and other desirable data. The electrophysiologic data, along with any other desirable data, may then be processed in any manner desirable, and assembled to produce any time-series electrophysiological signal(s). At process block 204, a parametric regression model may be generated, as described in Eqn. 2, which defines interference signal(s), as caused by periodic artifacts, using a harmonic representation.

At process block 206, the regression model may then be applied using the received electrophysiologic signal to define a cost function (Eqn. 7). In an iterative optimization process performed at process block 208, as described, estimates of regression parameters defined in the model may then be determined such that the cost function is reduced or minimized. The optimized regression parameters may then be used at process block 210 to determine interference signal(s), which then generate corrected electrophysiologic signal(s) at process block 212 by reducing, or removing, the interference signal(s) from the contaminated electrophysiologic signal(s). In particular, amplitudes, phases, and fundamental frequency for harmonics describing the interference signal are determined, along with amplitudes and phases of the underlying electrophysiologic signatures of interest in the electrophysiologic signal. At process block 214, a report representative of the corrected electrophysiologic signal, which may take any shape or form, as desired, may be generated. For example, the report may include one, two, or three-dimensional mapping, power spectra, spectrograms, coherograms, and so forth. In some aspects, corrected electrophysiologic signal(s) may also be combined with MRI data such as functional MRI ("fMRI") for instance, and other electrophysiologic data, such as ECG or GSR, and so on, to provide information about, or determine a clinical state of the subject, which may include indications regarding brain dynamics in behaviorally apparent or behavioral non-apparent cognitive and clinical states such as sleep, attention, coma, anesthesia, and epilepsy.

Figure 4A:
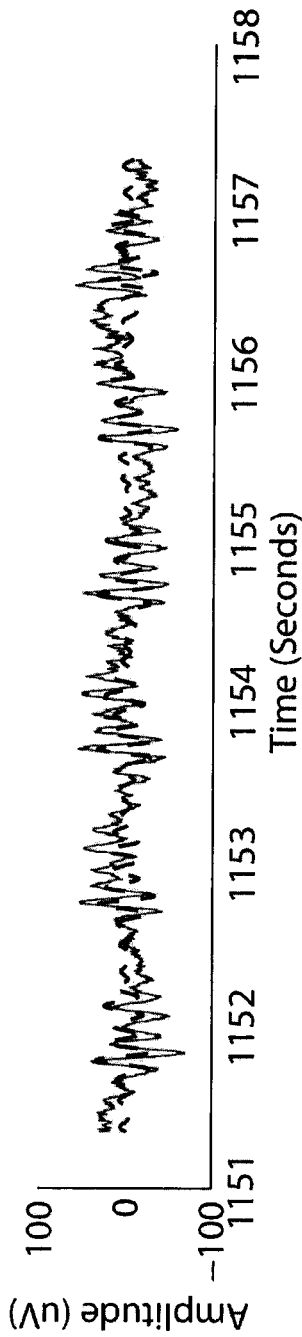
FIG. 4A-4B are graphical illustrations of example time domain corrupted EEG signals (FIG. 4A), estimates of BCG artifacts (FIG. 4A) and estimates of corrected EEG signals after removal of BCG artifacts (FIG. 4B), in accordance with the present invention.
Figure 4B:
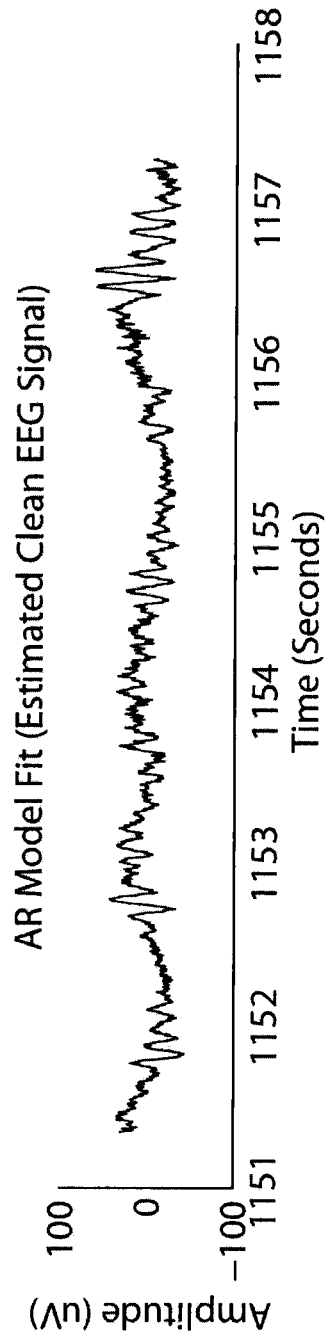

By way of example, FIGS. 3 and 4 show spectral and time domain estimates obtained using an approach applied, as detailed herein, on the BCG-corrupted EEG oscillation example acquired during general anesthesia (comparable to FIG. 1). Specifically, the panels of FIG. 3 illustrate how the approach of the present invention removes the BCG artifact to reveal oscillatory signatures of interest in an EEG recording within the MRI scanner. FIG. 4A overlays the BCG-corrupted EEG oscillation $y$ and the estimated BCG artifact (harmonic series $\hat{s}$) on a 3-second data segment. It is evident that the BCG artifact comprises a large proportion of the power in the corrupted EEG signal. FIG. 4B shows the estimated oscillatory component of the EEG (AR series $\hat{v}$), or in other words the electrophysiologic information of interest in the EEG. This oscillatory component has the 0-1 Hz and 8-12 Hz periodicities corresponding to known electrophysiologic signatures during general anesthesia. Thus clearly showing that the AR model described herein effectively recovers the temporal structure of the oscillatory signatures of interest in EEG signals.

Figure 5A:
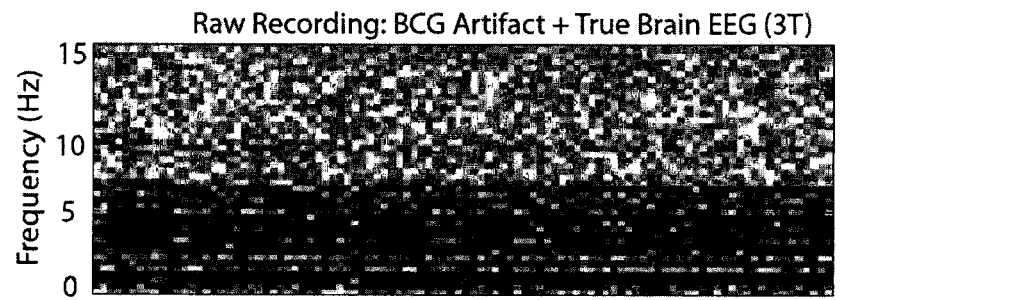
FIG. 5A-5C are graphical illustrations of example simulation tests to quantify improvement in the signal to noise ratio provided by the present invention, including spectrograms of raw corrupted EEG signals (FIG. 5A), true EEG signature of interest (FIG. 5B) and corrected EEG signals after removal of BCG artifacts (FIG. 5C), in accordance with the present invention.
Figure 5B:
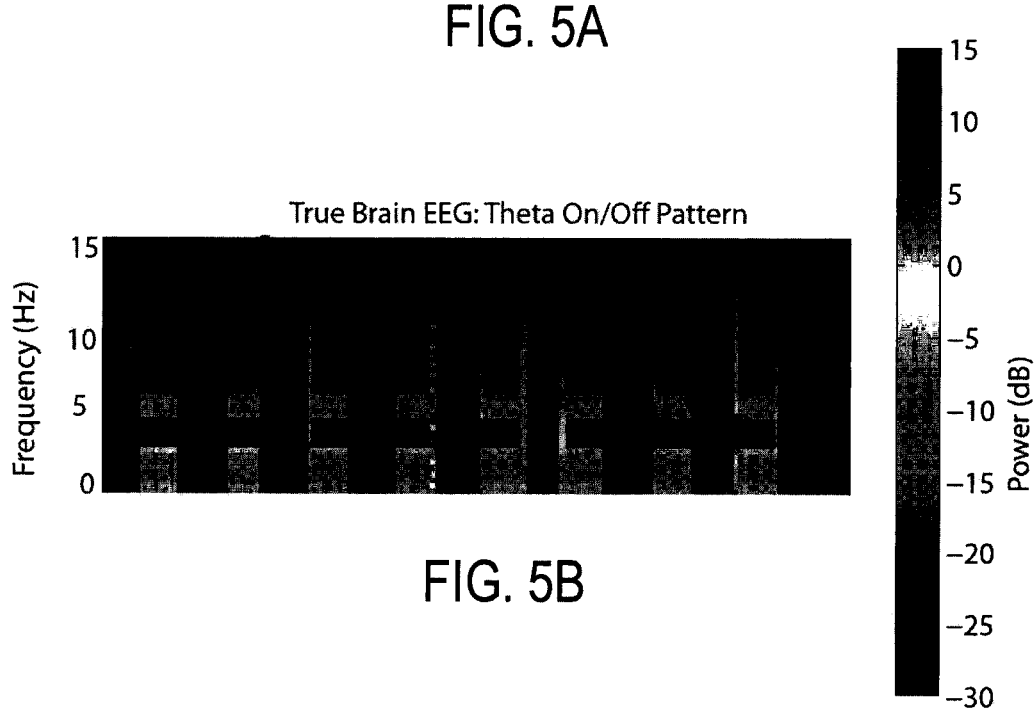
Figure 5C:
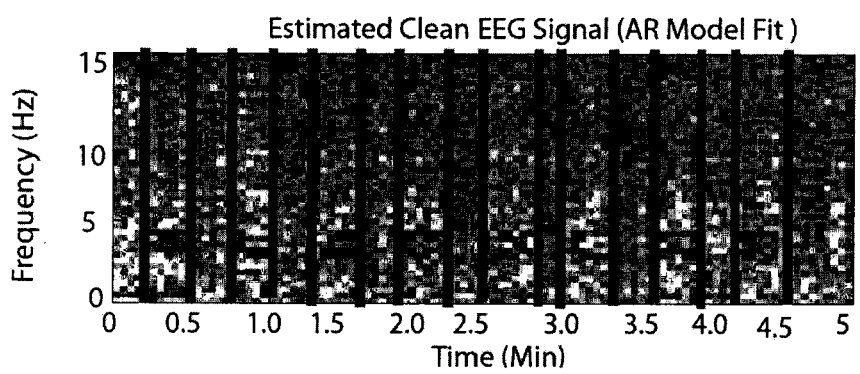
Figure 6A:
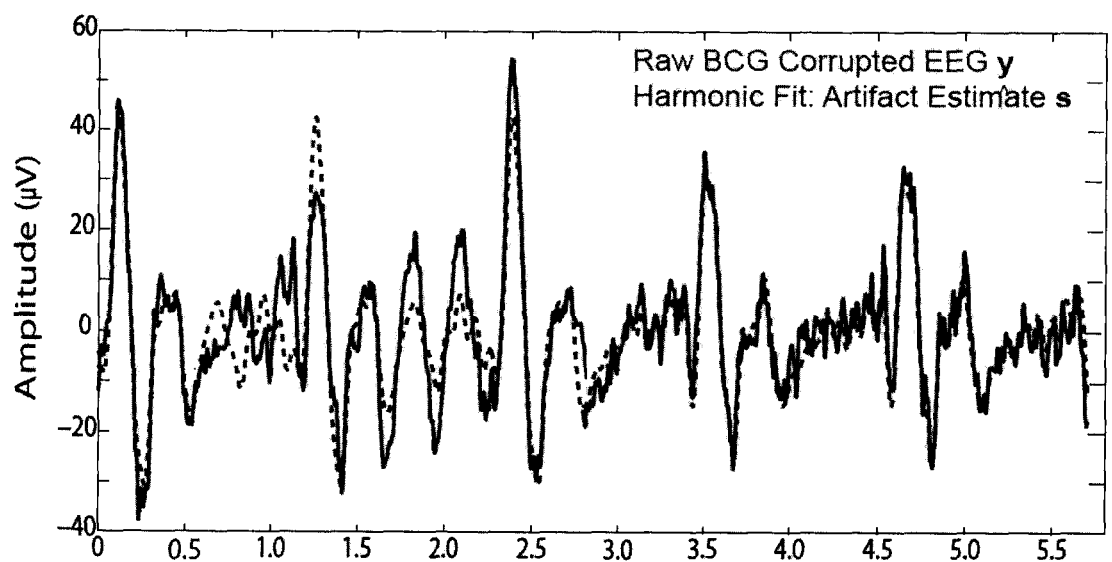
FIG. 6A-6B are graphical illustrations of example time domain corrupted EEG signals (FIG. 6A), estimates of BCG artifacts (6A) and estimates of corrected EEG signals after removal of BCG artifacts (FIG. 6B), in accordance with the present invention.
Figure 6B:
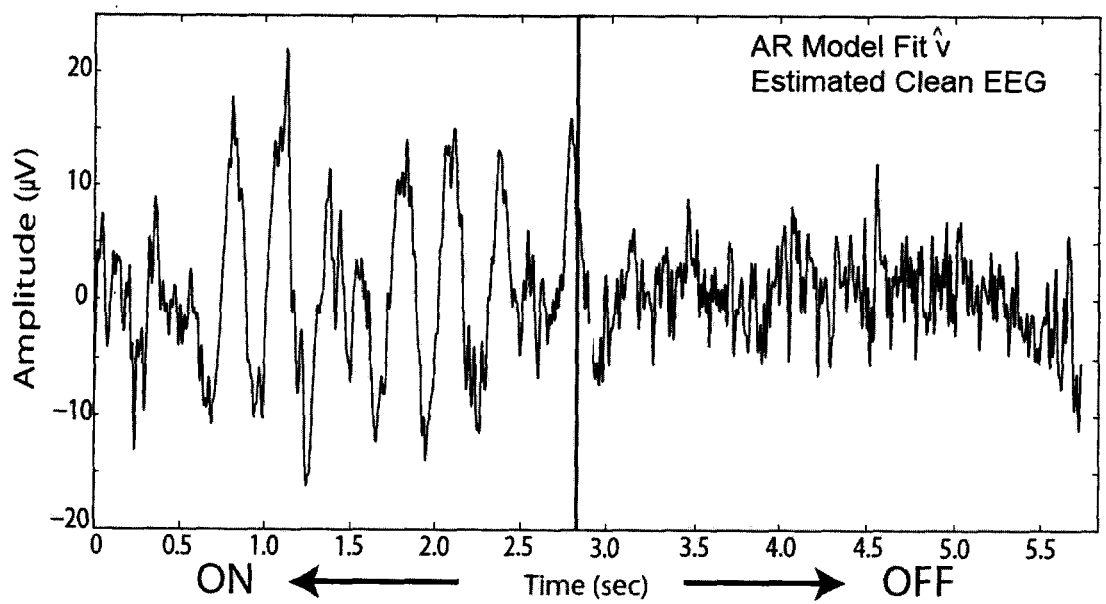

As an additional example, FIG. 5 and FIG. 6 illustrate a BCG-corrupted EEG oscillation test-case for benchmarking the performance of the algorithm detailed herein. Oscillatory and evoked response signals corresponding to brain-states of interest in studies of sleep, attention, anesthesia and epilepsy were generated and added on to resting state EEG recordings performed within a 3 Tesla MRI scanner. FIG. 5A illustrates the spectrogram of resting state EEG recording in the MRI scanner, while FIG. 5B illustrates the spectrogram of the simulated oscillatory component added on to the resting state recording of 5A. FIG. 5C illustrates the spectrogram of the cleaned EEG signal after removal of the BCG artifact with the present invention. The timing and periodicity of the simulated signal in 5B is preserved in 5C—thus clearly showing that the AR model described herein effectively preserves the temporal structure of the oscillatory signatures of interest in EEG signals. Time domain estimates corresponding to this test case are shown in FIG. 6—revealing the ability of the algorithm to uncover the ON/OFF pattern of the simulated oscillations. A variety of such test cases were performed—with simulated test signals spanning δ band (1-4 Hz), θ band (4-8 Hz), or α band (8-12 Hz), and comprised varying signal to artifact ratios (SNR). Across over 70 test cases for our model-based algorithm, the SNR improvement observed was consistently over 10-fold, which is significantly higher than the SNR improvement afforded by existing reference-based BCG removal methods.

Figure 7:
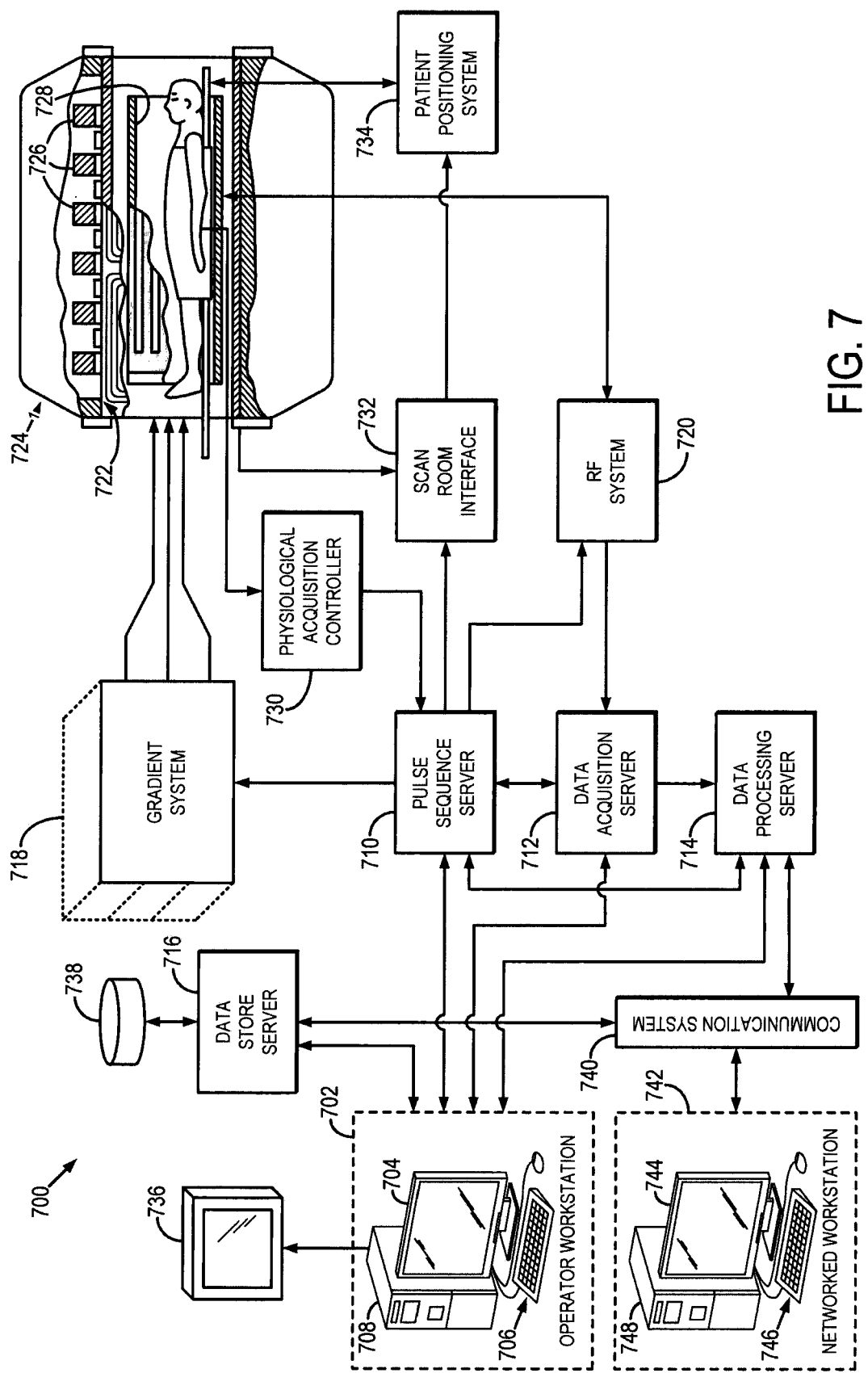
FIG. 7 is a block diagram of an example of a MRI system.

Referring particularly now to FIG. 7, an example of a magnetic resonance imaging ("MRI") system 700 is illustrated, suitable for use in accordance with the present invention. In one embodiment of the present invention, the MRI system 700 may be configured with capabilities for acquiring, processing and/or correcting EEG data, either intermittently or in real-time, and be able to estimate and remove, or reduce artifacts associated with the operation or environment created by the MRI system 700. For example, the MRI system 700 may be capable of estimating, reducing or removing interference signals produced by BCG artifacts from acquired EEG data.

The MRI system 700 includes an operator workstation 702, which will typically include a display 704; one or more input devices 706, such as a keyboard and mouse; and a processor 708. The processor 708 may include a commercially available programmable machine running a commercially available operating system. The operator workstation 702 provides the operator interface that enables scan prescriptions to be entered into the MRI system 700. In general, the operator workstation 702 may be coupled to four servers: a pulse sequence server 710; a data acquisition server 712; a data processing server 714; and a data store server 716. The operator workstation 702 and each server 710, 712, 714, and 716 are connected to communicate with each other. For example, the servers 710, 712, 714, and 716 may be connected via a communication system 740, which may include any suitable network connection, whether wired, wireless, or a combination of both. As an example, the communication system 740 may include both proprietary or dedicated networks, as well as open networks, such as the internet.

The pulse sequence server 710 functions in response to instructions downloaded from the operator workstation 702 to operate a gradient system 718 and a radiofrequency ("RF") system 720. Gradient waveforms necessary to perform the prescribed scan are produced and applied to the gradient system 718, which excites gradient coils in an assembly 722 to produce the magnetic field gradients $G_x$, $G_y$, and $G_z$ used for position encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil (not shown in FIG. 7), in order to perform the prescribed magnetic resonance pulse sequence. Responsive magnetic resonance signals detected by the RF coil 728, or a separate local coil (not shown in FIG. 7), are received by the RF system 720, where they are amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the scan prescription and direction from the pulse sequence server 710 to produce RF pulses of the desired frequency, phase, and pulse amplitude waveform. The generated RF pulses may be applied to the whole-body RF coil 728 or to one or more local coils or coil arrays (not shown in FIG. 7).

The RF system 720 also includes one or more RF receiver channels. Each RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 710 also optionally receives patient data from a physiological acquisition controller 730. By way of example, the physiological acquisition controller 730 may receive electrophysiologic signals from a number of different sensors connected to the patient, such as electrocardiograph ("ECG") signals from electrodes, or respiratory signals from a respiratory bellows or other respiratory monitoring device. Such signals are typically used by the pulse sequence server 710 to synchronize, or "gate," the performance of the scan with the subject's heart beat or respiration. In some aspects, capabilities to trigger or gate the performance of the scan may be enhanced by removing artifacts from the electrophysiologic signals received by controller 730.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, such that no data is lost by data overrun. In some scans, the data acquisition server 712 does lithe more than pass the acquired magnetic resonance data to the data processor server 714. However, in scans that require information derived from acquired magnetic resonance data to control the further performance of the scan, the data acquisition server 712 is programmed to produce such information and convey it to the pulse sequence server 710. For example, during prescans, magnetic resonance data is acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also be employed to process magnetic resonance signals used to detect the arrival of a contrast agent in a magnetic resonance angiography ("MRA") scan. By way of example, the data acquisition server 712 acquires magnetic resonance data and processes it in real-time to produce information that is used to control the scan.

The data processing server 714 receives magnetic resonance data from the data acquisition server 712 and processes it in accordance with instructions downloaded from the operator workstation 702. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 714 are conveyed back to the operator workstation 702 where they are stored. Real-time images are stored in a data base memory cache (not shown in FIG. 7), from which they may be output to operator display 712 or a display 736 that is located near the magnet assembly 724 for use by attending physicians. Batch mode images or selected real time images are stored in a host database on disc storage 738. When such images have been reconstructed and transferred to storage, the data processing server 714 notifies the data store server 716 on the operator workstation 702. The operator workstation 702 may be used by an operator to archive the images, produce films, or send the images via a network to other facilities.

The MRI system 700 may also include one or more networked workstations 742. By way of example, a networked workstation 742 may include a display 744; one or more input devices 746, such as a keyboard and mouse; and a processor 748. The networked workstation 742 may be located within the same facility as the operator workstation 702, or in a different facility, such as a different healthcare institution or clinic.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may exchanged between the data processing server 714 or the data store server 716 and the networked workstations 742, such that the data or images may be remotely processed by a networked workstation 742. This data may be exchanged in any suitable format, such as in accordance with the transmission control protocol ("TCP"), the Internet protocol ("IP"), or other known or suitable protocols.

Figure 8:
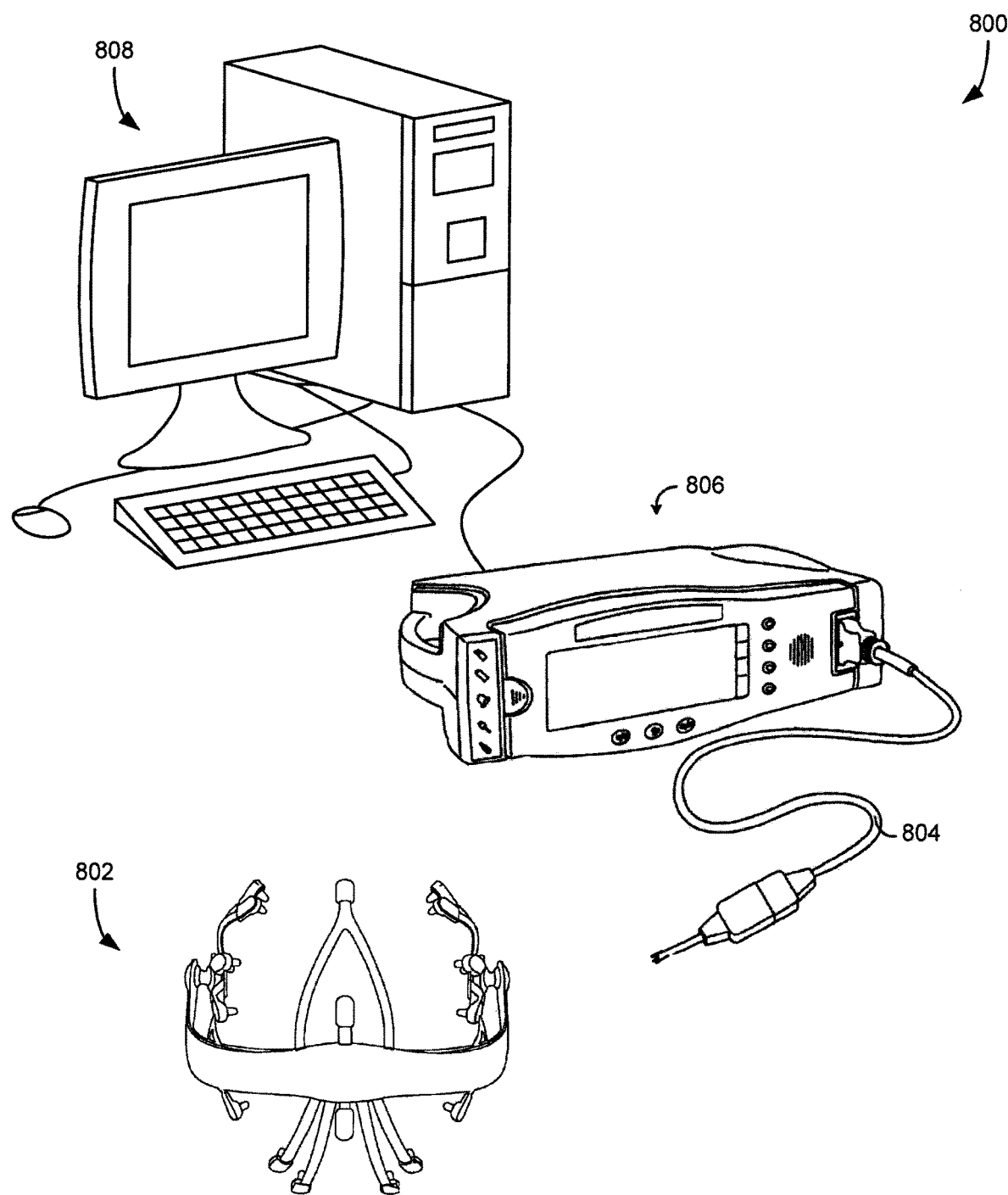
FIG. 8 is an illustration of an example monitoring system, in accordance with the present invention.

The physiological acquisition controller may include or be connected to a patient monitoring system, such as provided in FIG. 8. Likewise, as illustrated, the system of FIG. 8 may be a stand-alone system. Specifically, referring to FIG. 8, an exemplary system 800 in accordance with the present invention is illustrated. As noted, in some preferred aspects, the system 800 may configured for operation in proximity to a MRI environment and/or in cooperation or communication with a MRI system. In others, the system 800 may configured for independent operation.

The system 800 includes a patient monitoring device 802, such as a physiological monitoring device, or input, illustrated in FIG. 8 as an electroencephalography ("EEG") electrode array, which may include any number of sensors or electrodes arranged as desired on a subject. However, it is contemplated that the patient monitoring device 802 may also include mechanisms for monitoring galvanic skin response (GSR), for example, to measure arousal to external stimuli or other monitoring system such as heart-rate monitors, including electrocardiographic monitors and also ocular Microtremor monitors. One specific realization of this design may utilize a frontal Laplacian EEG electrode layout with additional electrodes to measure GSR. Another realization of this design may incorporate a frontal array of electrodes that could be combined in post-processing to obtain any combination of electrodes found to optimally detect the EEG signatures described earlier, also with separate GSR electrodes. Another realization of this design may utilize a high-density layout sampling the entire scalp surface, for example, using between 64 to 256 sensors, for the purpose of source localization, also with separate GSR electrodes.

The patient monitoring device 802 is connected via a cable 804 to communicate with a monitoring system 806. Also, the cable 804 and similar connections can be replaced by wireless connections between components. As illustrated, the monitoring system 806 may be further connected to a dedicated analysis system 808. Also, the monitoring system 806 and analysis system 808 may be integrated.

The monitoring system 806 may be configured to receive raw signals acquired by the EEG electrode array and assemble, and even display, raw or processed signals, as time-series EEG signals, or waveforms. Accordingly, the analysis system 808 may receive the EEG data from the monitoring system 806 and analyze the EEG data. In some preferred configurations, the analysis system 806 may be configured with capabilities for processing EEG data, either intermittently or in real-time, to determine and remove, or reduce artifacts in the time-series EEG signals, such as BCG artifacts, using an approach, as described herein. However, it is also contemplated that the functions of monitoring system 806 and analysis system 808 may be combined into a common system.

In some configurations, the analysis system 806 may be also configured to receive additional raw or processed data, such as MRI data acquired using a MRI system, and may be capable of combining the MRI data with raw or processed EEG data, as described. Based on such combinations, signature information or indications may be determined by the analysis system 806 in relation to brain cognitive and clinical states, such as sleep, attention, coma, anesthesia and epilepsy, or respiratory, autonomic or cardiac states of interest, among other information.

The analysis system 806 may then generate a report, for example, as a printed report or, preferably, a real-time display of raw or corrected time-series electrophysiologic signals, signature information and determined physiologic state of a subject. For instance, in studies of brain states, the report may include a real-time display of raw or corrected time-series EEG signals, signature information, determined brain state of a subject, and so forth.

In summary, the present invention provides systems and methods directed to estimating and removing artifacts, such as BCG artifacts, from corrupted electrophysiologic data recorded in conditions associated with MRI environments. Specifically, the present invention implements a harmonic regression technique that includes physically-motivated parametric models of BCG artifacts and true underlying EEG signals, and incorporates a local maximum likelihood approach to identify model parameters and estimate BCG artifacts, without need for acquiring reference signals or subjective case-specific criteria.

The approach of the present invention detailed herein was utilized to process and analyze a set of oscillatory BCG-corrupted EEG data recorded in MRI scanners at 3 Tesla and 7 Tesla to demonstrate the efficacy. It was shown that estimates provided by the present invention for oscillatory signatures of interest in the EEG reflect both overall pattern trends as well as specific timing and power changes of interest for cognitive and clinical studies. In addition, EEG oscillatory signatures estimated consistently resulted in over 10-20 fold increase in SNR over their BCG-corrupted counterparts. These results are unlike those obtained using reference-based methods which in some cases reduce SNR due to large residuals.

The present invention affords several novelties beyond current methods. Specifically, the technique presented adapts well to the time-varying nature of artifacts, and thus is uniquely suitable for long recording durations or studies using drugs where BCG features drift significantly. Particularly, in studies of brain states, the present invention may facilitate the use of EEG data obtained from fronto-temporal channels, which generally exhibit the worst artifacts, and is thus uniquely suitable for studies requiring data from those channels. Also, the present invention is amenable for real-time implementation, thus enabling continuous monitoring and online artifact removal. In addition, unlike other methods that perform less reliably due to worsening artifacts at high magnetic fields, the present invention is applicable for electrophysiologic data obtained at higher fields, capitalizing on the enhancement of artifact to signal ratio at higher fields. Hence, the approach of the present invention may be uniquely advantageous given the emerging preference for higher spatial resolutions afforded by high-field MRI techniques.

Moreover, unlike subtraction or basis decomposition techniques that require long segments of continuous contaminated recordings to estimate BCG artifacts, the present invention also works well on short data segments, as obtained, for example, during intermittent or interleaved recordings. In addition, the parametric model introduced may be well-poised to cope with time or stimulus dependent variations in BCG features.

In some envisioned applications, the present invention may facilitate enhanced monitoring of physiologic function in normal, clinical or pathological states. In the instance of brain function monitoring, the present invention enables correlations between (a) haemodynamic, biochemical or structural changes in brain, as measured by high spatial resolution MRI, and (b) concomitant high temporal resolution electrophysiologic signatures, using corrected EEG data processed to remove MR environment artifacts. In this manner, robust EEG-MRI acquisition and analysis may be performed, with the potential for research applications in neurophysiological and cognitive studies, and/or clinical applications in neurology, psychiatry and radiology. Specifically, the present invention may facilitate (a) diagnosis, pre-surgical evaluation, and treatment planning in epilepsy, (b) diagnosis and classification of coma and vegetative states, (c) psychophysical testing and cognitive assessments, (d) sleep studies, (e) neuropsychiatric drug research and (f) monitoring of disease progression or treatment response in a variety of neuropsychiatric conditions.

Features suitable for combinations and sub-combinations would be readily apparent to persons skilled in the art upon review of the present application as a whole. The subject matter described herein and in the recited claims intends to cover and embrace all suitable changes in technology.

The invention claimed is:

1. A magnetic resonance imaging ("MRI") system comprising:
   a magnet system configured to generate a polarizing magnetic field about a portion of the subject positioned in the MRI system;
   a plurality of gradient coils configured to apply a gradient field to the polarizing magnetic field;
   a radio frequency (RF) system configured to apply a RF excitation field to the subject, and
   acquire therefrom a set of magnetic resonance image ("MRI") data;
   at least one input configured to receive electrophysiologic data acquired from the subject;
   at least one computer configured to:
   a) process the electrophysiologic data as a time-series signal;
   b) apply a regression model that defines an interference signal caused by periodic artifacts in the time-series signal using a harmonic representation to define a cost function;
   c) perform an iterative optimization process to estimate regression parameters that minimize the cost function;
   d) determine, using the regression parameters, the interference signal;
   e) generate a corrected time-series electrophysiologic signal by reducing the interference signal relative to the time-series electrophysiologic signal; and
   wherein the cost function is defined as:

$$C(\omega, \beta, \alpha \mid y) = T\log\left(\frac{S_T}{T}\right) + \log(\det(Q)) + N;$$

wherein $S_T = (y - Z(\omega)\beta)^T Q^{-1}(y - Z(\omega)\beta)$ for an observed T×1 data vector of the time-series electrophysiologic signal, y, N is a number of harmonics in a spectrum of the time-series electrophysiologic signal, and $\omega$ (rad/sec) is a fundamental frequency defining a harmonic template, $\alpha$ and $\beta$ are the estimated parameters, Q is a covariance matrix and Z is a harmonic model matrix.

2. The system of claim 1, wherein the electrophysiologic data comprises electroencephalogram ("EEG") data.

3. The system of claim 1, wherein the regression model further defines oscillatory dynamics of an EEG signal by using an autoregressive representation.

4. The system of claim 3, wherein the at least one computer is further configured to determine a phase and an amplitude for signal components describing the EEG signal.

5. The system of claim 1, wherein the interference signal comprises a ballistocardiogram ("BCG") signal.

6. The system of claim 1, wherein the at least one computer is further configured to determine an amplitude, a phase, and a fundamental frequency for a number of harmonics describing the interference signal.

7. The system of claim 6, wherein the fundamental frequency is related to a heart rate.

8. The system of claim 1, wherein the at least one computer is further configured to perform the iterative optimization process by applying a cyclic descent technique.

9. The system of claim 1, wherein the at least one computer is further configured to combine the corrected time-series electrophysiologic signal with the set of MRI data to determine a physiologic state of the subject.

10. A system for monitoring a subject's brain, the system comprising:
   an input configured to receive electroencephalogram ("EEG") data acquired from a subject;
   at least one processor configured to:
      i) receive the EEG data from the input;
      ii) apply a regression model that defines a ballistocardiogram signal using a harmonic representation to the EEG data to define a cost function;
      iii) perform an iterative optimization process to estimate regression parameters that reduce the cost function;
      v) determine, using the regression parameters, the ballistocardiogram signal;
      vi) generate a corrected EEG data by reducing the ballistocardiogram signal within the EEG data;
   an output configured to deliver a report representative of the corrected EEG data; and
   wherein the cost function is defined as:

$$C(\omega, \beta, \alpha \mid y) = T\log\left(\frac{S_T}{T}\right) + \log(\det(Q)) + N;$$

wherein $S_T = (y - Z(\omega)\beta)^T Q^{-1}(y - Z(\omega)\beta)$ for an observed T×1 data vector of the time-series EEG data, y, N is a number of harmonics in a spectrum of the time-series EEG data, and ω (rad/sec) is a fundamental frequency defining a harmonic template, α and β are the estimated parameters, Q is a covariance matrix and Z is a harmonic model matrix.

11. The system of claim 10, wherein the regression model further defines oscillatory dynamics of an EEG signal by using an autoregressive representation.

12. A system for monitoring a subject's brain, the system comprising:
   an input configured to receive electroencephalogram ("EEG") data acquired from a subject;
   at least one processor configured to:
      i) receive the EEG data from the input;
      ii) apply a regression model that defines a ballistocardiogram signal using a harmonic representation to the EEG data to define a cost function;
      iii) perform an iterative optimization process to estimate regression parameters that reduce the cost function;
      v) determine, using the regression parameters, the ballistocardiogram signal;
      vi) generate a corrected EEG data by reducing the ballistocardiogram signal within the EEG data;
   an output configured to deliver a report representative of the corrected EEG data; and wherein the cost function is defined as:

$$C(\omega, \beta, \alpha \mid y) = T\log\left(\frac{S_T}{T}\right) + \log(\det(Q)) + N;$$

where is $S_T = (y - Z(\omega)\beta)^T Q^{-1}(y - Z(\omega)\beta)$ for an observed T×1 data vector of the EEG data, y, N is a number of harmonics in a spectrum of the EEG data as a time-series EEG signal, and ω (rad/sec) is a fundamental frequency defining a harmonic template, α and β are the estimated parameters, Q is a covariance matrix and Z is a harmonic model matrix.

13. The system of claim 10, wherein the at least one processor is further configured to determine an amplitude, a phase, and a fundamental frequency related to a heart rate, for a number of harmonics describing the ballistocardiogram signal.

14. The system of claim 10, wherein the at least one processor is further configured to combine the corrected EEG data with a set of functional magnetic resonance imaging (fMRI) data to determine a brain state of the subject.

15. A method for reducing artifacts in an electrophysiologic signal, the method comprising:
   receiving a time-series electrophysiologic signal acquired from a subject;
   providing a regression model that defines an interference signal caused by periodic artifacts using a harmonic representation;
   applying the regression model using the time-series electrophysiologic signal to define a cost function;
   performing an iterative optimization process to estimate regression parameters that minimize the cost function;
   determining, using the regression parameters, the interference signal;
   generating a corrected time-series electrophysiologic signal by reducing the interference signal;
   wherein the cost function is defined as:

$$C(\omega, \beta, \alpha \mid y) = T\log\left(\frac{S_T}{T}\right) + \log(\det(Q)) + N;$$

where is $S_T = (y - Z(\omega)\beta)^T Q^{-1}(y - Z(\omega)\beta)$ for an observed T×1 data vector of the electrophysiologic signal, y, N is a number of harmonics in a spectrum of the time-series electrophysiologic signal, and ω (rad/sec) is a fundamental frequency defining a harmonic template, α and β are the estimated parameters, Q is a covariance matrix and Z is a harmonic model matrix; and
   wherein the electrophysiologic signal is an electroencephalogram ("EEG") signal.

16. The method of claim 15, wherein the method further comprises acquiring the time-series electrophysiologic signal from a subject arranged within a MRI system.

17. The method of claim 15, wherein the regression model further defines oscillatory dynamics of an electrophysiologic signal by using an autoregressive representation.

18. The method of claim 15, wherein performing the iterative optimization process further includes determining an amplitude, a phase, and a fundamental frequency related to a heart rate for a number of harmonics describing the interference signal.

19. The method of claim 15, wherein performing the iterative optimization process further includes applying a cyclic descent technique.

20. The method of claim 15, wherein the method further comprises combining the corrected time-series electrophysiologic signal with a set of MRI data acquired using a MRI system to determine a physiologic state of the subject.

* * * * *

UNITED STATES PATENT AND TRADEMARK OFFICE
CERTIFICATE OF CORRECTION

PATENT NO. : 10,646,165 B2
APPLICATION NO. : 14/782479
DATED : May 12, 2020
INVENTOR(S) : Pavitra Krishnaswamy et al.

It is certified that error appears in the above-identified patent and that said Letters Patent is hereby corrected as shown below:

In the Specification

Column 5, Line 50, "$r^{1h}$" should be --$r^{th}$--.

Column 10, Line 61, "lithe" should be --little--.

Signed and Sealed this
Twenty-first Day of July, 2020

Andrei Iancu
*Director of the United States Patent and Trademark Office*